United States Patent
Vena et al.

(10) Patent No.: US 6,968,849 B2
(45) Date of Patent: Nov. 29, 2005

(54) METHOD, COMPOSITIONS, AND KITS FOR COLORING HAIR

(75) Inventors: Lou Ann Christine Vena, Scotch Plains, NJ (US); Saroja Narasimhan, Matawan, NJ (US); Maxine Gayle Moore, Piscataway, NJ (US); Glenn Robert Geardino, Edison, NJ (US); Manharbhai Kantibhai Patel, Saddlebrook, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 439 days.

(21) Appl. No.: 10/270,915

(22) Filed: Oct. 15, 2002

(65) Prior Publication Data

US 2004/0016064 A1 Jan. 29, 2004

Related U.S. Application Data

(60) Provisional application No. 60/397,346, filed on Jul. 19, 2002.

(51) Int. Cl.$^7$ ............................................. A61K 7/13
(52) U.S. Cl. .......................................... 132/208; 8/405
(58) Field of Search ................. 132/208, 200, 132/202; 8/405, 423, 406, 407, 408

(56) References Cited

U.S. PATENT DOCUMENTS

| | | | |
|---|---|---|---|
| 4,775,527 A | 10/1988 | Bires et al. ................. 424/62 |
| 4,834,767 A | 5/1989 | Helioff et al. ............... 8/416 |
| 4,957,731 A | 9/1990 | Helioff et al. .............. 424/62 |
| 5,224,964 A | 7/1993 | Shami ........................ 8/405 |
| 5,560,750 A | 10/1996 | Crews et al. ................ 8/431 |
| 5,575,989 A | 11/1996 | Caskey ...................... 424/62 |
| 5,635,461 A | 6/1997 | Onitsuka et al. ........... 510/126 |
| 3,912,446 A | 10/1997 | Zviak ....................... 8/10.1 |
| 5,674,476 A | 10/1997 | Clausen et al. ............. 424/62 |
| 5,688,291 A | 11/1997 | Said et al. .................. 8/431 |
| 5,725,600 A | 3/1998 | Caisey et al. ................ 8/103 |
| 5,891,423 A | 4/1999 | Weeks ....................... 424/62 |
| 5,980,587 A | 11/1999 | Samain ....................... 8/426 |
| 5,989,530 A | 11/1999 | Lorenz et al. .............. 424/62 |
| 6,045,591 A | 4/2000 | Deneulenaere ............... 8/426 |
| 6,206,935 B1 | 3/2001 | Onitsuka et al. ............. 8/431 |
| 6,440,177 B1 | 8/2002 | Orr ........................... 8/426 |
| 6,596,035 B2 | 7/2003 | Gutkowski et al. .......... 8/10.1 |
| 2003/0154562 A1 | 8/2003 | Sarojini ..................... 8/405 |

OTHER PUBLICATIONS

Zviak, Charles. The Science of Hair Care. Marcel Dekker, Inc., pp. 214–277.
wwwglobalcosmetic.com (GCI), Sep. 2002, pp. 61 and 62.
Maxim, Permanent Hair Color for Men, circa Jan. 1, 2000.
L'Oréal Feria, Colour Strands, Quick Shimmer Bleach Blast C90, circa Jan. 1, 2000.

Primary Examiner—John J. Wilson
Assistant Examiner—Robyn Kieu Doan
(74) Attorney, Agent, or Firm—Julie Blackburn

(57) ABSTRACT

A method for altering the color of hair comprising applying a bleach composition containing persulfate salts and at least one oxidizing agent to the desired strands of hair for a period of time sufficient to bleach the hair, removing the bleach composition from the hair but leaving at least some residual oxidizing agent on the bleached hair strands, then treating the hair with a colorant composition containing at least one dye operable to color hair in the presence of the residual oxidizing agent found on the bleached hair strands, said colorant composition being free of any oxidizing agents operable to react with the dye present therein to form color, whereby upon contact with the colorant composition, the hair strands treated with the bleach composition having residual oxidizing agent thereon will react with the dye present in the colorant composition to cause the bleached hair strands to become colored, while any remaining unbleached hair will not become colored by contact with the colorant composition and a kit and shampoo composition for use with the method.

27 Claims, 6 Drawing Sheets

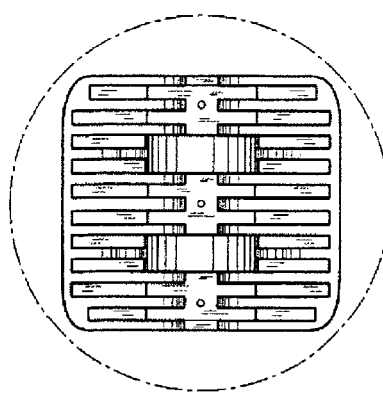
FIG. 2
FIG. 3A
FIG. 2A
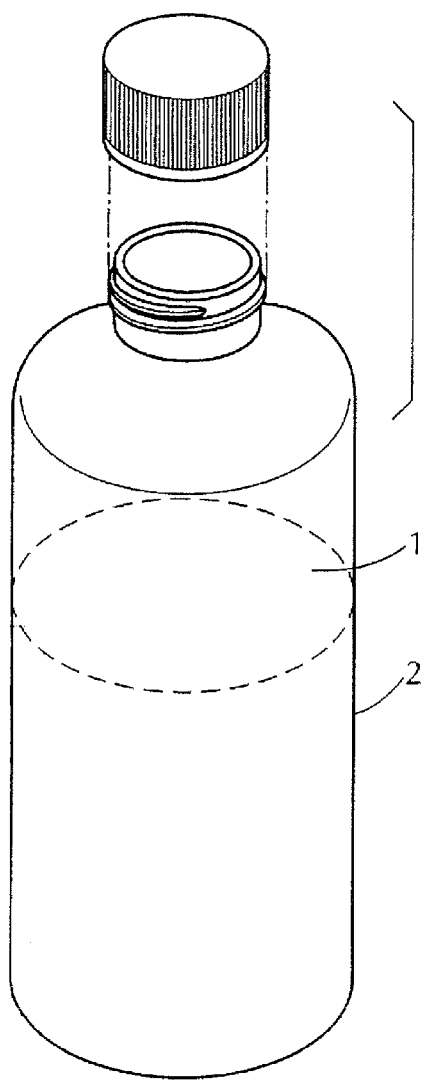
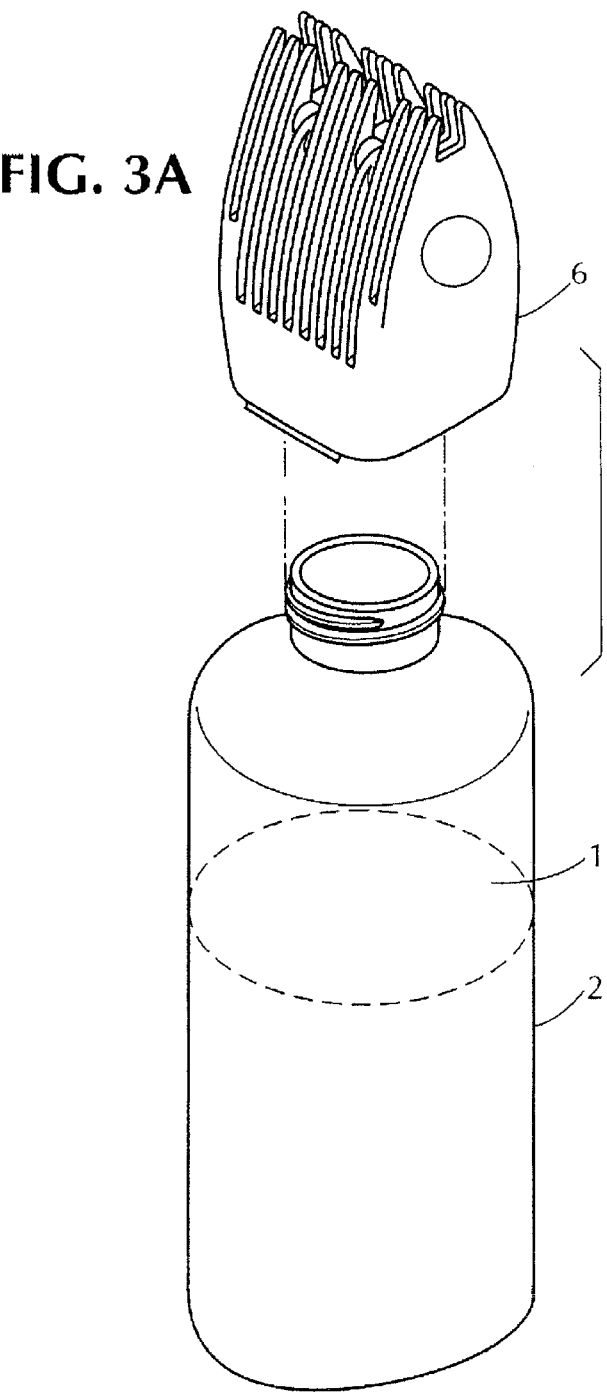

FIG. 4
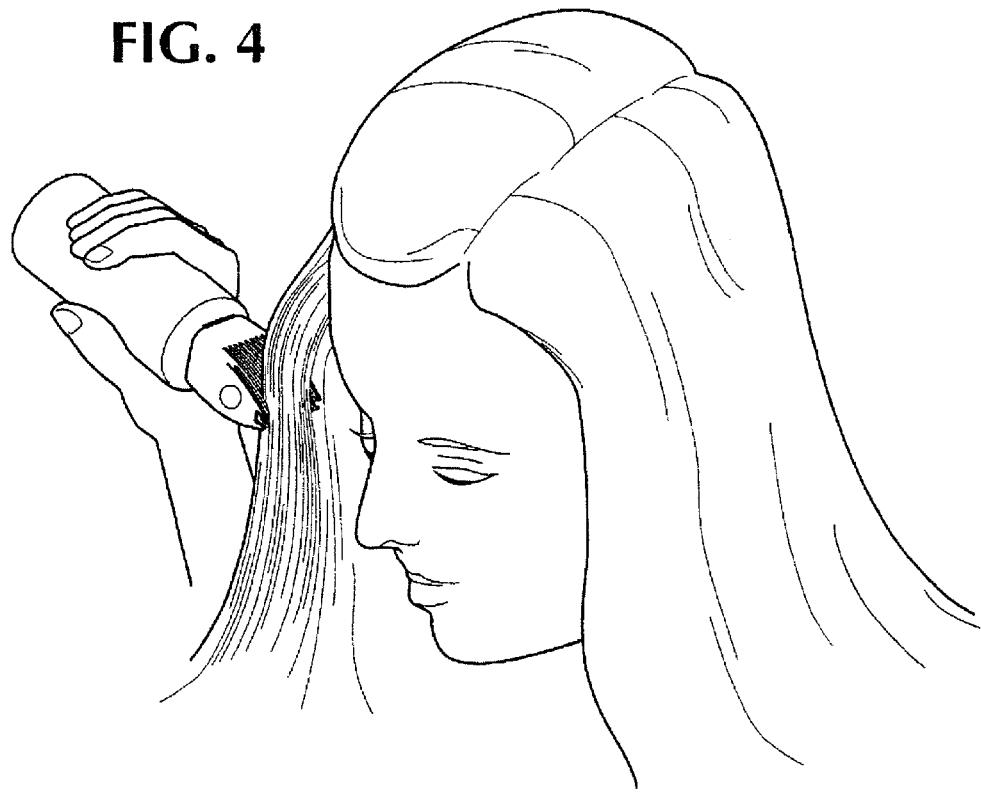
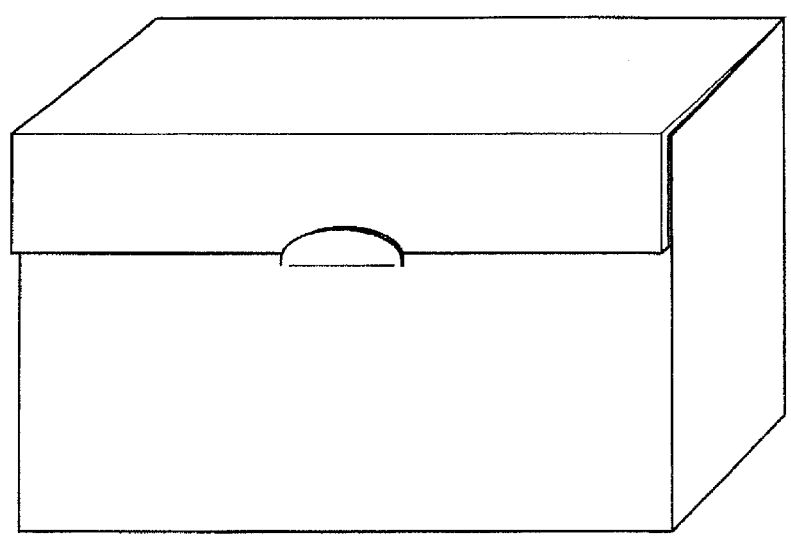
FIG. 5A

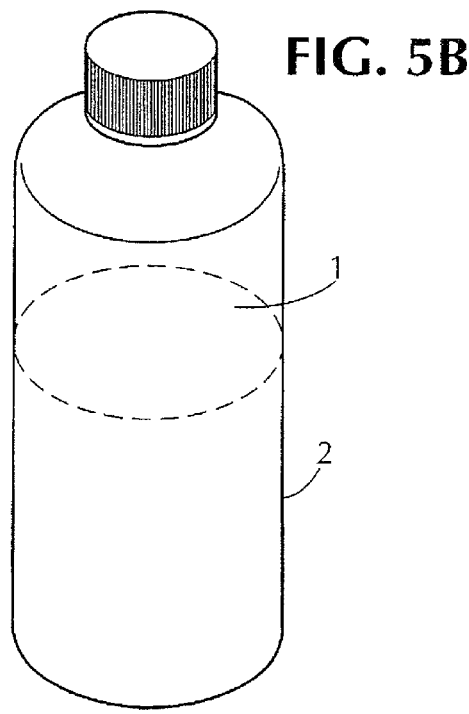
FIG. 5B
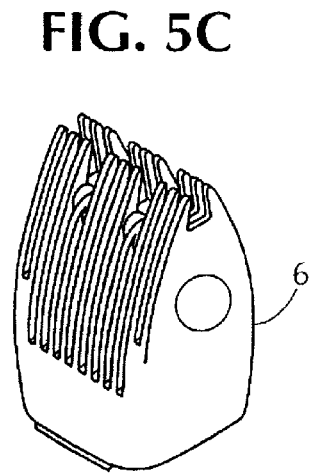
FIG. 5C
FIG. 5D
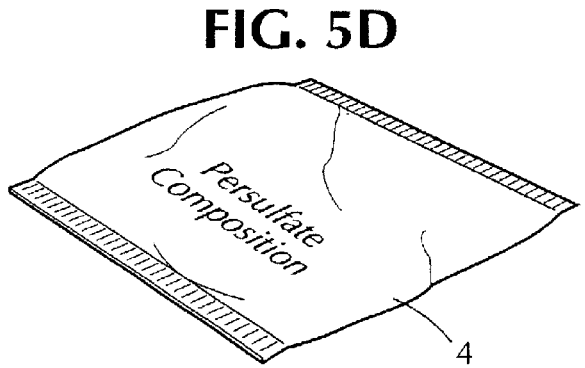
FIG. 5E
FIG. 5F
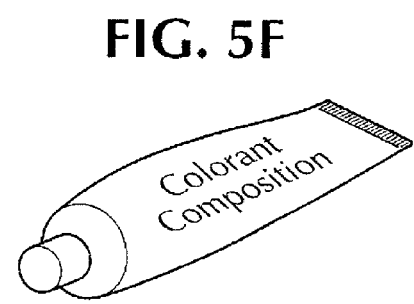
FIG. 5G
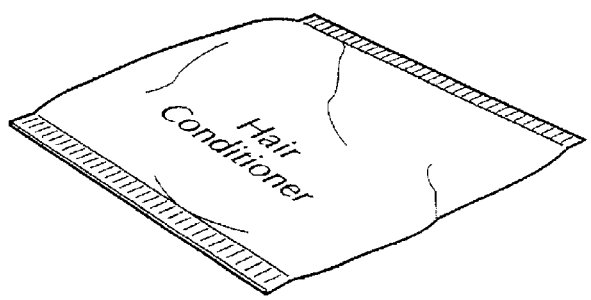

METHOD, COMPOSITIONS, AND KITS FOR COLORING HAIR

This application claims priority from provisional patent application Ser. No. 60/397,346, filed Jul. 19, 2002.

TECHNICAL FIELD

The invention is in the field of coloring hair, including applying highlights to hair.

BACKGROUND OF THE INVENTION

Highlights are very popular with consumers today. Highlights involve bleaching select strands of hair to achieve a color that is different (usually lighter) than the color of the base hair shade. This in turn provides unique effects such as a sun kissed look on an individual with dark blonde hair, or possibly lighter brown streaks on a black haired individual.

In beauty salons, highlights are expensive. Generally the entire process takes from one to three hours. Typically strands of hair selected for highlighting are arranged on many small pieces of metal foil which are positioned throughout the hair based upon the judgment of the beautician. The strands on the foil are painted with the highlighting, or bleach, composition (a mixture of a persulfate composition and an oxidizing agent composition) for the appropriate period of time after which the foils are individually removed from the hair and it is rinsed well with water to remove all traces of the highlighting composition. The placement of the foil pieces is a very time consuming, labor intensive process that requires a certain judgment and skill, and when that is considered along with the time required for the actual bleaching operation, the entire process becomes quite lengthy and difficult.

Alternatively, plastic caps referred to as streaking caps may be used. These are plastic caps similar to bathing caps that have holes pierced throughout in a pattern determined by the manufacturer. The beautician pulls small strands of hair through the holes. The highlighting composition is applied to the select strands of hair for the desired period of time, generally about 30 to 60 minutes, then rinsed with water.

Thereafter, in both cases, the hair is washed with shampoo to remove the excess highlighting composition, or simply rinsed well with water. In some cases, a second process is performed which involves treating the entire head of hair with a mild oxidative hair color to reduce the brassiness, or fine tune the color, of the highlights. At the same time the non-bleached hairs are colored by the mild oxidative hair color as well. In prestige beauty salons, highlighting procedures can cost several hundred dollars or more.

It is also possible for consumers who do not wish to pay salon prices to use the at home kits that are available for purchase in drug and mass market stores. However, due to the level of skill involved in applying highlights, it is more difficult to obtain professional salon looking results when using at home kits. Typically these kits include a plastic cap pierced with holes in a predetermined pattern. The consumer pulls the hair through the holes with a device that looks somewhat like a crochet hook. The select hairs are then treated with the highlighting composition for a period of time ranging from 30 to 60 minutes. The hair is rinsed with water and shampooed. There are several problems with the at-home kits. First, the manufacturer determines the pattern of the holes in the cap, providing a one-size-fits all approach. Thus, the pattern tends to be very standard and not at all tailored to each individual consumer. Further, the process of putting on a plastic cap that feels and looks much like a bathing cap, and then pulling hair strands through the holes in the cap with a crochet-hook like instrument is very labor intensive. Combining the time required for that exercise with the time required for the bleach to act on the hair, results in a process that easily takes more than one to two hours. Another type of retail bleaching kit contains a small comb that the consumer manually uses to distribute the highlighting composition on the hair. These systems are messy, and the color application is often not uniform as there tends to be too much color at the hair roots and not enough at the ends.

There are many drawbacks to the current highlighting procedures whether conducted in the salon or at home. The actual bleaching process, which involves bleaching melanin or color from the hair fiber, provides inconsistent results. This is true whether the whole head is being bleached or only select strands (the latter being referred to as "highlighting"). Ideally, one would want to treat the hair with a composition containing bleach and hair dye to simultaneously bleach the melanin from the hair fibers, and color the hair fibers the desired color. However, because the ingredients used in the bleach (oxidizing agent and persulfate salts) are very reactive with oxidative hair dyes, when such ingredients come into contact they immediately react and the reactants are consumed before anything productive can be done with the mixture. In some cases, the hair is first bleached to remove melanin. Then a second procedure is commenced where the same hair strands that have been treated with bleach are oxidatively dyed. This is obviously a very cumbersome and time consuming procedure that is not easily implemented in either the salon setting or in at home kits, and it could cause hair damage in those who have chemically over-processed hair.

Accordingly, one of the biggest need gaps in the highlighting or bleaching process is to provide bleached or highlighted hair that is the desired color, not just whatever color is achieved when the melanin is bleached from hair fibers, in a simple but effective procedure that is amenable to salon or at home use.

Another significant problem with standard bleaching or highlighting procedures is that they are not effective on hair that has already been color treated. Thus, such procedures are not possible for the many consumers that have already colored their hair because it is very difficult to bleach hair that has been colored with oxidative dye.

Accordingly, there is a need for a process and compositions that provide a consumer friendly, speedy system for bleaching the entire head of hair or highlighting select strands which provides custom colored highlights with salon quality results. This system should be able to provide consistent results in lightening and coloring virgin hair as well as hair that has already been oxidatively colored. While the system can be used at home or in the salon, it is most desirable that the system be amenable for use in at-home kits by standard consumers.

Accordingly, it is an object of the invention to provide a method for bleaching or highlighting hair that provides custom color, meaning that the color is the one desired by the consumer and correlates to the color charts depicted on the package in which the product is sold.

Another object of the invention is to provide a method for bleaching or highlighting hair that enables coloration in a reduced period of time.

Another object of the invention is to provide a method for bleaching or highlighting hair that has already been treated with oxidative or semi-permanent dyes.

Another object of the invention is to provide a method for bleaching or highlighting hair that provides consistent results on virgin hair as well as hair that has been treated with oxidative or semi-permanent dyes, or bleaches.

Another object of the invention is to provide a method for bleaching or highlighting hair where the compositions can be applied to dry hair.

Another object of the invention is to provide a method for bleaching or highlighting hair that provides professional salon results in an at-home, consumer friendly process.

Another object of the invention is to provide a shampoo composition for treating hair comprising one or more primary intermediates and, if appropriate, couplers for the formation of oxidation dyes, but which is free of oxidizing agents which react with the intermediates and couplers, if present, to color the hair.

SUMMARY OF THE INVENTION

The invention is directed to a method for altering the color of hair comprising applying a bleach composition containing persulfate salts and at least one oxidizing agent to the desired strands of hair for a period of time sufficient to bleach the hair, removing the bleach composition from the hair but leaving at least some residual oxidizing agent on the bleached hair strands, then treating the hair with a colorant composition containing at least one dye operable to color hair in the presence of the residual oxidizing agent found on the bleached hair strands, said colorant composition being free of any oxidizing agents operable to react with the dye present therein to form color, whereby upon contact with the colorant composition, the hair strands treated with the bleach composition having residual oxidizing agent thereon will react with the dye present in the colorant composition to cause the bleached hair strands to become colored, while any remaining unbleached hair will not become colored by contact with the colorant composition.

The invention is also directed to a kit for applying highlights to hair comprising (i) a first receptacle containing a oxidizing agent composition, (ii) a second receptacle containing a persulfate composition, (iii) a comb through applicator attachable to the first receptacle or the second receptacle; and (iv) a third receptacle containing a colorant composition free of oxidizing agents but containing at least one oxidative dye reactive with the oxidizing agent in the first receptacle composition.

The invention is also directed to a shampoo composition for treating or cleansing hair comprising one or more primary intermediates and, if appropriate, couplers for the formation of oxidation dyes, but being free of oxidizing agents which react with the primary intermediate and coupler, if present, to form color on the hair when the shampoo composition is applied thereto.

BRIEF DESCRIPTION OF THE DRAWINGS

FIG. 2: is a top plan view of the comb through applicator affixed to the container of FIG. F which illustrates the orifices through which the bleach composition exudes when the comb on applicator is stroked through the hair strands.

FIG. 3A: is an exploded view of the receptacle and comb through applicator illustrating how the comb through applicator is affixed to the container after removal of the lid 2A affixed to the receptacle for storage purposes.

FIG. 4: illustrates the use of the device depicted in FIG. 1F to apply the bleach composition to select strands of hair.

FIGS. 5A–F: generally depicts the kit of the invention and the various components found therein.

FIG. 5A: depicts a box, which is one container that may be used to store the various components of the kit of the invention.

FIG. 5B: depicts the receptacle used to store the oxidizing agent composition.

FIG. 5C: shows the comb through applicator that is found in the kit in the preferred embodiment of the invention, although the other comb through applicators depicted in FIGS. 1E through 1F may be used as well.

FIG. 5D: shows the persulfate composition, which is in the packette form in this drawing, but may be stored in other forms as set forth in FIGS. 3B, 3C, and 3D in FIG. 3.

FIG. 5E: shows the hair conditioner composition which is an optional component of the kit.

FIG. 5F: shows the colorant composition that is found in the kit depicted here in a tube receptacle.

FIG. 5G: shows another type of receptacle for containing the optional hair conditioner composition found in the kit. This is a packette form.

DETAILED DESCRIPTION

Figure 1A:
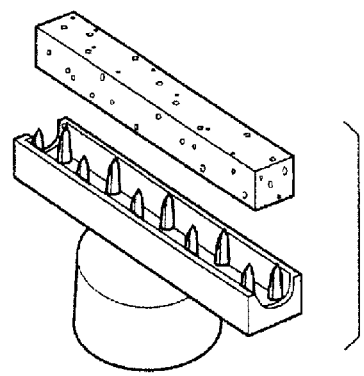
FIG. 1A: depicts one type of comb through applicator that may be used in the method and kit of the invention.
Figure 1B:
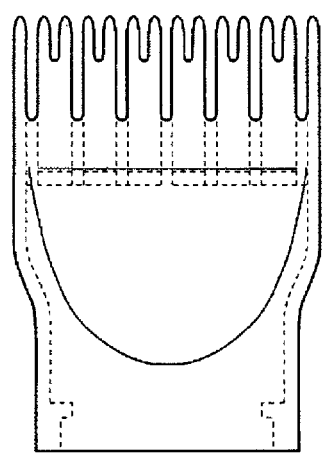
FIG. 1B: depicts another type of comb through applicator that may be used in the method and kit of the invention.
Figure 1C:
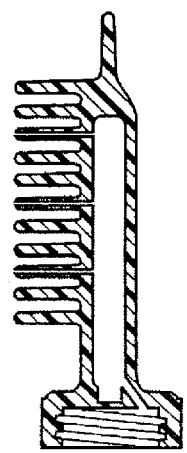
FIG. 1C: depicts another type of comb through applicator that may be used in the method and kit of the invention.
Figure 1D:
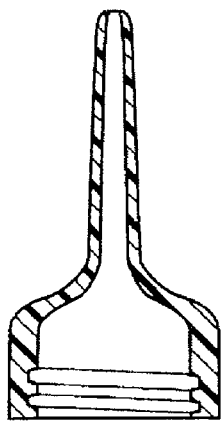
FIG. 1D: depicts another type of comb through applicator that may be used in the method and kit of the invention.
Figure 1F:
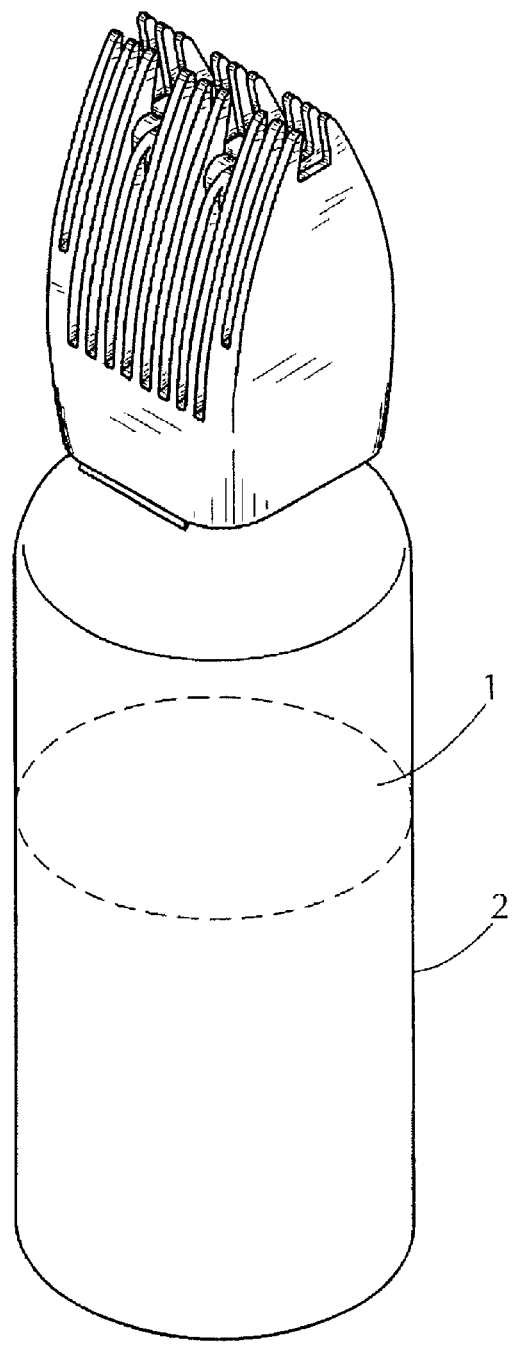
FIG. 1F: illustrates the preferred type of comb applicator attached to a receptacle for use in the method and kit of the invention.
Figure 1E:
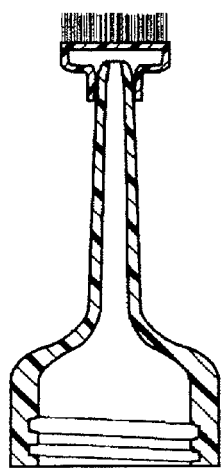
FIG. 1E: depicts another type of comb through applicator that may be used in the method and kit of the invention.

The invention is directed to a very user friendly fast, and convenient method for providing salon quality highlights to virgin hair or hair that has already been colored with oxidative or semi-permanent hair color. While in the preferred embodiment of the invention the method and kit are used to apply highlights to the hair (e.g. to alter the color of only select strands of hair), the claimed method and kit can be used to bleach or color the entire head of hair as well. In the latter case, the method provides a faster, more effective way to alter the color of hair and the results are more consistent.

The method is very adaptable for at home use. It is possible to obtain the desired color and the procedure can be used on dry hair. The process eliminates much of the inconsistency in the current bleaching or highlighting procedures. The ability to use oxidative dyes in a bleaching or highlighting procedure adds another level to the bleach process. The bleached hair strands can be treated with the desired highlighting color rather than color that is obtained when the melanin is bleached from the hair fibers. This provides more tailored, custom color that can be designed for each specific consumer's coloring and taste and also eliminates the brassy hair color that is sometimes seen when hair is simply bleached to remove melanin from the hair.

The Method

1. Application of the Bleach Composition

The first step of the method comprises the application of a bleach composition comprised of a mixture of persulfate salts and at least one oxidizing agent to select hair strands. The hair strands may be selected in any suitable manner so long as the hairs to be treated with bleach are segregated from those for which highlights are not intended. It is possible that the consumer may want to treat the entire head of hair, and if so the claimed method is suitable for that purpose.

In the event highlights are desired, the preferred method for applying the bleach composition to select hair strands will be further described herein. If desired, processes for segregating hair strands to be highlighted can use foil pieces or the plastic cap with perforations as well as any other type of comb on or brush on device, or simply digital application. The bleach composition is applied to the select strands of hair for the desired period of time, usually about 5 to 65 minutes, preferably about 10 to 45 minutes. The composition is then removed from the hair strands, preferably by rinsing well with water. It is important that the bleach composition be removed sufficiently so as not to negatively impact the second step which involves application of the colorant composition, but at the same time the removal must be such that residual oxidizing agent from the bleach process is left remaining on the hairs that were treated with the bleach composition.

In the preferred embodiment of the invention, the composition containing the persfulate salts and the aqueous oxidizing agent composition are combined in standard proportions, for example about 10 to 90 parts of the oxidizing agent composition are combined with about 10 to 90 parts of the persulfate composition. Preferably about 50–95 parts of the oxidizing agent composition are combined with about 15–50 parts of the persulfate composition. The combination of ingredients is mixed well and applied to the strands of hair that are selected for highlighting. As discussed above, the hair to be highlighted can be selected in any manner desired although it is preferred that the types of applicators depicted in FIGS. 1A through 1F be used as the delivery device. In particular, the oxidizing agent composition will be found in the container depicted in FIGS. 1 and 3. The oxidizing agent composition 1 is preferably stored in a receptacle 2 with a lid 2A (see FIG. 3). Preferably, the receptacle 2 is made from a plastic material that is inert to the ingredients that are found in the oxidizing agent composition. The receptacle 2 has a lid 2A (shown removed from the receptacle 2 in FIG. 3) which is affixed to the receptacle to close it when the container 2 is stored. When the consumer desires to begin the coloring procedure, the lid 2A is removed from the receptacle 2 and the persulfate composition which may be stored in a packette 4 or tube 5 or any other suitable storage receptacle, is poured into the receptacle 2 containing the oxidizing agent composition 1. In the case where the persulfate composition is in the form of a powder, the packette 4 form is preferable. Where the persulfate composition is in the form of a paste, the tube 5 may be a suitable storage receptacle. Preferably, the consumer then replaces the lid 2A on the receptacle 2 and shakes it well to mix the contents. After the receptacle contents are mixed well, the comb through applicator 6 (or any other desired comb through applicator, further examples of which are set forth in FIGS. 1A through 1E) is affixed to the receptacle 2 and the oxidizing agent/bleach mixture is applied to the hair by combing the comb through applicator through the hair strands as depicted in FIG. 4. When the comb applicator is stroked downwardly through the hair strands, the bleach/oxidizing agent mixture is automatically applied to select hair strands to create a very natural highlighting effect without the necessity of segregating select hair strands and separately treating those strands. In fact, the comb through applicator is so easy to use that even when users are not skilled in the highlighting or bleaching process the results are excellent. The user needs simply to comb the applicator through the hair using the usual combing movements and the bleach composition will apply to the individual strands of hair in an acceptable manner.

The preferred comb through applicator and receptacle are further disclosed in U.S. provisional patent application Ser. No. 60/397,472, filed on Jul. 19, 2002, naming inventors Louann Christine Vena, Saroja Narasimhan, Maxine Gayle Moore, Glenn Robert Geardino, and Manharbhai Kantibhai Patel and entitled "Cosmetic Applicator and Storage Container" and the corresponding non-provisional utility patent application filed on the same date as this non-provisional utility patent application, having the same title and inventors; and U.S. design patent application Ser. No. 29/164,215, filed Jul. 19, 2002, entitled "Cosmetic Applicator", naming Louann Christine Vena, Saroja Narasimhan, Maxine Gayle Moore, Glenn Robert Geardino, and Manharbhai Kantibhai Patel as co-inventors. Both the provisional and non-provisional utility and design patent applications are hereby incorporated by reference herein in their entirety, including the drawings.

The mixture is left on the hair for a time sufficient to cause the hair to be bleached. This time period may range from about 10 to 60 minutes depending on the effect desired by the consumer and the color of the consumer's hair prior to beginning the method. Preferably the time period ranges from about 10 to 30 minutes.

After the appropriate period of time has passed, the bleach mixture is removed from the hair, preferably by rinsing well with water for a time and in a manner that adequately removes the bleach composition but leaves the hairs treated with the bleach composition with residual oxidizing agent present thereon. Rinsing for a period of time ranging from about 1 second to about 5 minutes is generally sufficient to adequately remove the bleach composition and still leave the treated hair strands containing residual oxidizing agent. Preferably the hair should be rinsed for a period of time ranging from about 3 seconds to 4 minutes, most preferably about 3 seconds to about 2 minutes.

The bleach composition and the ingredients used therein in the preferred embodiment of the invention will be further described.

2. The Bleach Composition

The term "bleach composition" when used herein means a composition that is applied to the hair to bleach melanin, and any previously applied dyes that are in the hair, out of the hair fibers. It is obtained by combining a persulfate salt containing composition and an oxidizing agent composition prior to intended use of the composition. The term "persulfate salt composition" means a composition that contains persulfate salts which are operable to bleach hair when combined with an oxidizing agent. The term "oxidizing agent composition" means a composition that contains at least one oxidizing agent that is operable to react with the persulfate salts to form an active composition that is capable of bleaching melanin from hair fibers.

(a). The Persulfate Composition

A variety of persulfate compositions may be suitable, including those well known in the art. The persulfate composition may be in the powdered particulate or paste form and in general may have one or more of the ingredients set forth below. The persulfate composition preferably comprises a mixture of persulfate salts that are capable of bleaching the hair when combined with an oxidizing agent, particulate fillers, and, if desired, inorganic particulate colorants. The persulfate composition used in the claimed method may be found in the powdered particulate form, or in the form of a cream or paste as described in U.S. Pat. No. 5,888,484; and U.S. patent application Ser. No. 09/774,890, filed Feb. 1, 2001, assigned to Revlon Consumer Products Corporation, naming Teresita Imperial as inventor, both of which are hereby incorporated by reference in their entirety. The typical ingredients found in the persulfate composition are further described herein.

(i). Persulfates

The persulfate composition comprises about 10–65%, preferably about 20–60%, more preferably about 25–55% by weight of the total bleach composition of one or more inorganic persulfates which may be alkali metal or alkaline earth metal persulfates, or ammonium persulfate. Preferably the persulfate composition comprises one or more of an alkali metal, alkaline earth metal, or ammonium persulfate. Examples of alkali metal persulfates include lithium, sodium, potassium, cesium, and the like. Examples of suitable alkaline earth metals include magnesium, calcium, and the like. Particularly preferred are sodium, potassium, and ammonium persulfates. The persulfates are generally in particulate form and have particle sizes ranging from about 0.1 to 200 microns. The persulfates should be reactive with the hydrogen peroxide or the other peroxide oxidizing agent present in the oxidizing agent composition when the persulfate composition is combined with the oxidizing agent composition.

(ii). Alkalizing Agents

The persulfate composition preferably contains one or more alkalizing agents. Preferred alkalizing agents are one or more inorganic salts as set forth herein. Suggested ranges of inorganic salts are from about 0.1–40%, preferably about 0.5–35%, preferably about 1–30% by weight of the total composition.

(iii). Particulate Fillers

The persulfate composition also preferably comprises one or more particulate fillers. Preferably, the bleach composition comprises about 5–60%, preferably about 8–55%, more preferably about 10–50% by weight of the total bleach composition of the particulate fillers. The term "particulate filler" means a generally inert particulate having a particle size of about 0.1–250 microns. The particulate fillers provide volume and, when mixed with the persulfates, dilute the persulfate particles. A variety of particulate fillers are suitable including inorganics, inorganic salts, hydrophilic colloids, carbohydrates, soaps, alkyl sulfates, and the like.

(aa) Inorganics

Examples of inorganics include silica, hydrated silica, alumina, attapulgite, bentonite, calcium oxide, chalk, diamond powder, diatomaceous earth, fuller's earth, hectorite, kaolin, mica, magnesium oxide, magnesium peroxide, montmorillonite, pumice, talc, tin oxide, zeolite, zinc oxide, and the like.

(bb) Hydrophilic Colloids

Examples of suitable hydrophilic colloids include hydroxyethylcellulose, locust bean gum, maltodextrin, methylcellulose, agar, dextran, dextran sulfate, gelatin, pectin, potassium alginate, sodium carboxymethylchitin, xanthan gum, and the like.

(cc) Carbohydrates

Examples of suitable carbohydrates include sugars such as glucose, sucrose, maltose, xylose, trehelose, and derivatives thereof, in particular sugar esters of long chain, $C_{14-30}$ fatty acids, as well as dextrins, cellulosics, and derivatives thereof.

(dd) Soaps and Alkyl Sulfates

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

(iv). Inorganic Colorants

If desired, the persulfate composition may comprise about 0.01–2%, preferably about 0.05–1%, more preferably about 0.1–1% by weight of the total persulfate composition of an inorganic colorant. The inorganic colorant is preferably in the particulate form and will provide a subtle coloration to the powder composition to make it more aesthetically pleasing for commercial purposes. Particularly preferred for use in the persulfate composition is ultramarine blue.

(v). Lipophilic Ingredients

It may be desirable to include one or more lipophilic ingredients in the persulfate composition. If so, suggested ranges of the lipophilic ingredient are from about 0.1–70%, preferably about 0.5–60%, more preferably about 1–50% by weight of the total composition. Suitable lipophilic ingredients include liquids, solids, or semi-solids at room temperature (25° C.). Examples of such lipophilic ingredients include silicone oils, organic oils, fatty acids, fatty alcohols, hydrocarbons, paraffins, silicone waxes, and the like.

(b) The Oxidizing Agent Composition

The oxidizing agent composition is preferably aqueous based and if so may be in the solution or emulsion form. If the latter, the emulsion may be in the water-in-oil or oil-in-water form. Further, the emulsion may also be in the microemulsion form, if desired.

When the aqueous oxidizing agent is in the solution form the composition preferably comprises about 1–30% by weight of the total composition of an oxidizing agent, preferably hydrogen peroxide, and about 70–99% by weight of the total composition of water. Other water soluble ingredients may be included in the solution, such as humectants, preservatives, water soluble thickeners, antioxidants, and so on.

When the aqueous oxidizing agent composition is in the emulsion form, the composition preferably comprises about 1–30% of oxidizing agent, preferably hydrogen peroxide, about 50–99% water, and about and 0.01–30%, preferably about 0.05–20%, more preferably about 0.1–15% of an oily phase. The aqueous oxidizing agent composition may be in the form of a water-in-oil or oil-in-water emulsion or in the form of a transparent microemulsion wherein the dispersed particles in the continuous phase are so small (generally about 5–1500 Å) that the composition is optically clear. Examples of suitable microemulsion compositions are set froth in U.S. Pat. No. 6,315,989, which is hereby incorporated by reference in its entirety. It is also suitable that the aqueous oxidizing agent composition be in the form of a composition containing liquid crystals as set forth in U.S. Pat. No. 6,238,653, which is hereby incorporated by reference in its entirety.

The various ingredients that may be found in the aqueous oxidizing agent composition (also referred to as "developer") are as follows.

(i). Oxidizing Agent.

Preferably the oxidizing agent is hydrogen peroxide, although other suitable peroxides such as urea peroxide, sodium perborate, etc. may be used as well. Preferably the aqueous oxidizing agent composition contains hydrogen peroxide.

(ii). Lipophilic Ingredients

The lipophilic oil may be present in the aqueous oxidizing agent composition if this composition is in the emulsion form. If so, suggested ranges are about 1–85%, preferably about 3–70%, preferably about 5–65% by weight of the total composition. The lipophilic ingredients that are suitable for use in one embodiment of the persulfate composition are also suitable for use in the oxidizing agent composition.

(iii). Humectants

Humectants may be present in the aqueous oxidizing agent composition. If so, suggested ranges are from about 0.01–10%, more preferably about 0.05–8%, most preferably about 0.1–5% by weight of the total composition of humectant. Suitable humectants include monomeric, homopolymeric, and/or block copolymeric ethers as well as mono-, di-, or polyhydric alcohols.

Suitable ethers are formed by the polymerization of monomeric alkylene oxides, generally ethylene or propylene oxide. Such polymeric ethers have the following general formula:

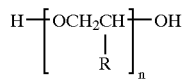

wherein R is H or lower alkyl and n is the number of repeating monomer units, and ranges from 1 to 500.

Also suitable are polyols such as glycerine or $C_{1-4}$ alkylene glycols and the like. Particularly preferred are $C_{1-4}$ alkylene glycols, in particular propylene and/or butylene glycol and ethoxydiglycol.

Suitable mono-, di-, or polyhydric alcohols include glycerin, butylene glycol, ethylene glycol, propylene glycol, and so on.

(v). Water Soluble Thickeners

The aqueous oxidizing agent composition may contain one or more water soluble thickeners. If present suggested ranges are from about 0.1–25%, preferably about 0.5–20%, more preferably 1–15% by weight of the total composition. Suitable thickeners include.

(aa) Acrylic Copolymer Thickeners

Suitable acrylic copolymeric thickeners are comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. Preferably, the thickening agent is a polymer comprised of A, B, and C monomers wherein A and B are as defined above, and C has the general formula:

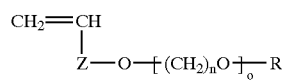

Preferably, in the copolymer used for the secondary thickening agent in the preferred embodiment of the invention, A and B are as above defined; and in the C monomer Z is $(CH_2)_m$, m is 1–2, n is 2, and o is 2–100, and R is a $C_{12-22}$ straight or branched chain alkyl. More preferably in the C monomer m is 1, n is 2, o is 10, and R is $C_{18}$ or stearyl, and the compound is steareth-10 allyl ether/acrylate copolymer, which may be purchased from Allied Colloids under the tradename Salcare SC90.

Also suitable is an aqueous solution of an acrylic polymer comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer with the remainder water. The composition of the acrylic copolymer may contain from about 0.1–99 parts of the A monomer, and about 0.1–99 parts of the B monomer. Preferably, the acrylic copolymer contains enough of the A monomer to enable ionization in a basic solution, thereby causing the ionized carboxylic acid groups in the polymer to repel each other, and thereby "swallow" water. Particularly preferred acrylic copolymer solutions suitable for use in the developer composition include those sold by Seppic, Inc., under the tradename Capigel, in particular, Capigel 98, which is a white liquid having a pH of 2 to 4, a solids content of about 29–31, a density of 1.04 to 1.08, and a viscosity of 700–1000 millipascal seconds at 25° C.

(bb) Associative Thickeners

Various other types of associative thickeners may be present, including water soluble urethane homo- and copolymers, and the like.

(vi). Nonionic Surfactants

If desired, the oxidizing agent composition may contain one or more nonionic surfactants. Recommended ranges are 0.01–10%, preferably 0.05–8%, more preferably 0.1–7% by weight of the total composition. Suitable nonionic surfactants include those set forth below.

(aa) Alkoxylated Alcohols

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on.

(bb) Alkoxylated Carboxylic Acids

Also suitable as the nonionic surfactant are alkyoxylated carboxylic acids, which are formed by the reaction of a carboxylic acid with an alkylene oxide or with a polymeric ether. The resulting products have the general formula:

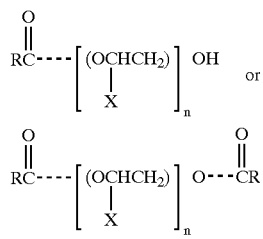

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

(cc) Sorbitan Derivatives

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

The aqueous oxidizing agent composition may also comprise a variety of other ingredients including cationic, amphoteric, or zwitterionic surfactants, preservatives if desired.

3. Removal of the Bleach Composition

After the select strands of hair have been treated for the desired period of time to cause the melanin to be bleached from the hair, the bleach composition is removed from the hair. Preferably this is accomplished by rinsing the hair with water to remove all traces of the bleach composition. The objective is to remove as much of the bleach composition as possible but leave the treated hair strands having residual oxidizing agent thereon. Preferably, the hair is rinsed with water for about 1 second to 5 minutes. Most preferably, the hair should be rinsed with water for about 5 to 25 seconds. Even with strenuous rinsing, residual amounts of the oxidizing agent that was present in the bleach composition will remain on the treated strands, and in particular enough of the residual oxidizing agent to be reactive with the dye contained in the colorant composition to enable coloration of the bleached hair strands.

4. Application of the Colorant Composition

After the hair has been rinsed well with water, the colorant composition is applied to the hair for a period of time sufficient to react with only the treated strands of hair to form color thereon. In particular, the colorant composition is free of oxidizing agents but contains at least one dye that is reactive with the oxidizing agent that was used in the aqueous oxidizing agent composition, and which is found in residual amounts on the hair fibers that were bleached with the bleach composition. Because the colorant composition does not contain any oxidizing agents, it is not operable to color hair by itself because the dye present is not activated by contact with oxidizing agents as in a normal hair coloring procedure. Instead, when the colorant composition, which is free of oxidizing agents, is applied to the entire head of hair, the dye present in that composition will react with the residual oxidizing agent that is left on the treated hair fibers. The treated hair fibers will become colored, but the untreated hairs will remain uncolored because they contain no residual oxidizing agent and the hair colorant composition itself contains no oxidizing agent so it is not operable by itself to color the hair. Preferably, the colorant composition is in the form of a shampoo so that the consumer can simply shampoo the hair for the desired period of time after the bleach has been rinsed from the hair. Most conveniently, the colorant composition is applied to the entire head of hair, rather than just the bleached strands, yet the oxidative dyes found therein will be reactive only with the bleached hair strands having residual oxidizing agent thereon, and will not have any impact on the untreated hair.

The colorant composition may contain a variety of ingredients in addition to the dye that is present.

5. The Colorant Composition

The colorant composition contains at least one oxidative dye, either alone or in combination with a coupler for the formation of oxidation dyes and, preferably, other ingredients. Preferably the colorant composition is an aqueous form, comprising from about 0.1–99% water in combination with the at least one dye. The composition may be in the solution or emulsion form. Suitable dyes are preferably oxidative dyes and include at least one primary intermediate and at least one coupler for the formation of oxidation dyes. Most preferred is where the colorant composition is in the form of a shampoo which is used by the consumer to shampoo the hair after the bleaching procedure has been completed.

(a). Primary Intermediates.

The colorant composition preferably comprises one or more primary intermediates. Suggested ranges of primary intermediates are about 0.0001–6%, preferably about 0.0005–5.5%, more preferably about 0.001–5% by weight of the total composition. Such primary intermediates are well known for use in hair color, and include ortho or para substituted aminophenols or phenylenediamines, such as para-phenylenediamines of the formula:

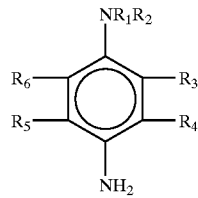

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4- diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

(b). Color Coupler

Preferably the colorant composition comprises from about 0.0001–10%, more preferably about 0.0005–8%, most preferably about 0.001–7% by weight of the total composition of one or more color couplers. Suitable color couplers include, for example, those having the general formula:

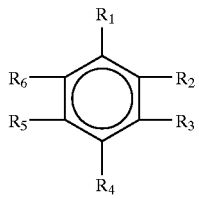

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methylpyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3 [(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino) benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Preferred color couplers include resorcinol, 1-naphthol, 2-methylresorcinol, 4-amino-2-hydroxy toluene, m-aminophenol, 2,4-diaminophenoxyethanol, phenyl methylpyrazolone, their salts, or mixtures.

The colorant composition may also comprise a variety of other ingredients to enhance the aesthetics and efficacy thereof, as further set forth herein.

(c) Other Ingredients (i). Surfactants or Emulsifiers

Preferably, the colorant composition comprises one or more surfactants that assist in maintaining the composition in the preferred emulsion form and aid in the foaming capability of the composition. Suitable surfactants include anionic surfactants, nonionic surfactants, amphoteric surfactants, and the like.

(aa) Nonionic Surfactants

Suggested ranges of nonionic surfactant are about 0.01–10%, preferably about 0.05–8%, more preferably about 0.1–7% by weight of the total composition. Suitable nonionic surfactants include alkoxylated alcohols or ethers, alkoxylated carboxylic acids, sorbitan derivatives, and the like, as mentioned for use with the oxidizing agent composition set forth above.

(bb) Anionic Surfactants

Preferably, the hair colorant composition is in the shampoo form and comprises one or more cleansing surfactants such as anionic surfactants. Preferred ranges of anionic surfactant are about 0.1–25%, preferably about 0.5–20%, more preferably 1–15% by weight of the total composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1\text{—}SO_3\text{—}M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

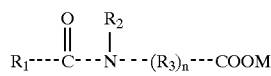

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Also suitable are amphoteric and zwitterionic surfactants. Examples of amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

(ii). Thickening Agents

Preferably the colorant composition contains one or more thickening agents that increase the viscosity of the composition such that when it is applied to hair it doesn't run. The amount of thickening agent, if present, is about 0.001–5%, preferably about 0.005–4%, more preferably about 0.005–3% by weight of the total composition.

A variety of thickening agents are suitable including low melting point waxes, carboxyvinyl polymers, cellulosic thickeners (such as hydroxypropyl cellulose, hydroxypropyl methylcellulose), and the like. Particularly preferred thickening agents are cellulosic thickeners, either alone or in combination with low melting point waxes such as emulsifying wax, fatty alcohols (e.g. stearyl alcohol, cetearyl alcohol, behenyl alcohol, and the like).

(iii) Alkalizing Agents

The colorant composition may contain one or more alkalizing agents. If present, the suggested range is about 1–5% based on the total weight of the colorant composition. The term "alkalizing agent" means an ingredient that is capable of imparting alkalinity (e.g. a pH of greater than 7) to the colorant composition. Suitable alkalizing agents include ammonium hydroxide, metal hydroxides, alkanolamines, sodium silicate, metal carbonates, sodium metasilicate, and mixtures thereof. Suitable metal hydroxides and carbonates include alkali metal and alkaline earth metal hydroxides or carbonates. Examples of such metal hydroxides include sodium, potassium, lithium, calcium, magnesium and so on. A particularly preferred alkaline earth metal hydroxide is sodium hydroxide. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof. A particularly preferred alkanolamine is MEA.

The alkalizing agent present in the colorant composition may react with other ingredients in the mixture in situ, such as fatty acids, proteins or hydrolyzed proteins, and the like. Depending on the amount of alkalizing agent present and the presence or absence of ingredients that will react with the alkalizing agent, it is possible that the alkalizing agent may be completely reacted in situ, partially reacted in situ, or not reacted at all if there are no other ingredients in the composition that will react with the alkalizing agent.

(iv). Fatty Acids

The colorant composition may contain one or more fatty acids, and if so suggested ranges are about 0.001–15%, preferably 0.005–10%, most preferably 0.01–8% by weight of the total composition. If fatty acids are present they will react with the alkalizing agent to form soap in situ, which provides a more shampoo-like character to the aqueous hair color composition once it is applied to hair. Such fatty acids are of the general formula RCOOH wherein R is a straight or branched chain, saturated or unsaturated $C_{6-30}$ alkyl. Examples of suitable fatty acids include oleic acid, stearic acid, isostearic acid, myristic acid, linoleic acid, and so on. Particularly preferred is oleic acid or isostearic acid.

(v). Solvents

It may be desirable to include one or more solvents in the colorant composition. Such solvents assist in solubilizing the primary intermediate and coupler ingredients, in addition to the other ingredients in the composition. The solvent is preferably present at about 0.01–10%, preferably about 0.05–8%, more preferably about 0.1–7% by weight of the total composition. Suitable solvents include $C_{2-4}$ alkanols such as ethanol, isopropanol, propanol, etc., glycols such as butylene glycol, propylene glycol, ethylene glycol, glycerin and the like as well as derivatives thereof; as well as ethoxyglycols. The preferred solvent comprises ethoxydiglycol.

(vi). Chelating Agents

Preferably, the colorant composition contains one or more chelating agents that are capable of chelating the metal ions found in water. If water contains too many extraneous metal ions they can interfere with the coloration process. Preferred ranges of chelating agent are 0.001–5%, preferably 0.005–4%, more preferably 0.01–3% by weight of the total composition. Preferred chelating agents are EDTA, HEDTA, and sodium or potassium salts thereof.

(vii). Antioxidants, Preservatives

The colorant composition may also contain one or more antioxidants or preservatives, as are known in the art. Suitable ranges of such ingredients are preferably from about 0.0001–6% by weight of the total composition.

(viii). Conditioners

The colorant composition may comprise one or more conditioners that exert a conditioning effect on hair. A variety of conditioners are suitable including cationic polymers, oily conditioning agents, fatty alcohols, proteins, and so on. A combined total weight of conditioners ranges from about 0.1–25%, preferably 0.5–20%, more preferably 1–15% by weight of the total composition.

(aa) Cationic Polymers

A variety of cationic polymers are suitable such as quaternary derivatives of cellulose ethers or guar derivatives, copolymers of vinylpyrrolidone, polymers of dimethyldiallyl ammonium chloride, acrylic or methacrylic polymers, quaternary ammonium polymers, and the like.

(i) Quaternary Derivatives of Cellulose

Examples of quaternary derivatives of cellulose ethers are polymers sold under the tradename JR-125, JR-400, JR-30M. Suitable guar derivatives include guar hydroxypropyl trimonium chloride.

(ii) Copolymers of Vinylpyrrolidone

Copolymers of vinylpyrrolidone having monomer units of the formula:

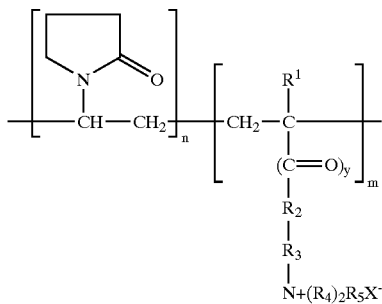

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—$CHOH$—$CH_2$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(iii) Polymers of Dimethyldiallylammonium Chloride

Homopolymers of dimethyldiallylammonium chloride, or copolymers of dimethyldiallylammonium chloride and acrylamide are also suitable. Such compounds are sold under the tradename MERQUAT by Calgon.

(iv) Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use.

(v) Polymeric Quaternary Ammonium Salts

Also suitable are polymeric quaternary ammonium polymers such as Polyquaternium 10, 28, 31, 33, 34, 35, 36, 37, and 39.

(vi) Diquaternary Polydimethylsiloxanes

Also suitable are diquaternary polydimethylsiloxanes such as Quatemium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby (bb) Oily Conditioning Agents Also suitable are a variety of oily materials that provide good conditioning effect to hair. Suitable oils are liquid at room temperature and may comprise esters, hydrocarbons, and the like. Preferably the composition comprises 0.001–20%, more preferably 0.005–15%, most preferably 0.01–10% by weight of the total composition of such oils. Particularly preferred oily conditioning agents are oils extracted from vegetable sources.

(cc) Nonionic Silicones

Also suitable as conditioning agents are one or more silicones. Suitable silicone hair conditioning agents include volatile or nonvolatile nonionic silicone fluids, silicone resins, and silicone semi-solids or solids.

Volatile silicones are linear or cyclic silicones having a measureable vapor pressure, which is defined as a vapor pressure of at least 2 mm. of mercury at 20° C. Examples of volatile silicones are cyclic silicones having the general formula:

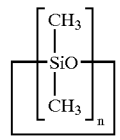

where n=3–7.

Also, linear volatile silicones that may be used in the compositions of the invention have the general formula:

where n=0–7, preferably 0–5.

The colorant composition may comprise water insoluble nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

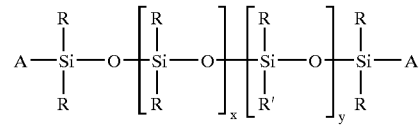

wherein R and R' are each independently alkyl, aryl, or an alkyl substituted with one or more amino groups, and x and y are each independently 0–100,000, with the proviso that x+y equals at least one and A is siloxy endcap unit. Preferred is where A is methyl, R is methyl, and R' is an alkyl substituted with at least two amino groups, most preferably an amine-functional silicone having the formula:

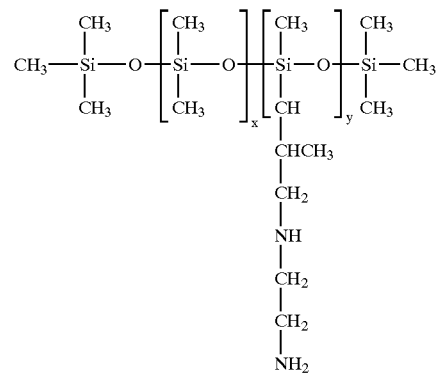

which is known by the CTFA name trimethylsilylamodimethicone.

The silicone hair conditioning agent may also be a silicone polymer having the following general formula:

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, each of which is a blend of about 40–60% volatile silicone and 40–60% trimethylsiloxy silicate. Dow Corning 2-0749, in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Particulary preferred is where the colorant composition is a shampoo which contains, by weight of the total composition, about:

0.0001–6% of at least one primary intermediate, 0.1–25% of an anionic surfactant, 0.001–5%, of a thickening agent.

Additionally, the shampoo composition may contain one or more of the ingredients, and in the suggested ranges, as set forth above.

After the hair is treated for the desired period of time with the hair colorant composition, the hair is rinsed well with water to remove the colorant composition. The hair that was treated with the bleach and hair colorant composition has been altered while the hair that was not treated with the bleach composition remains unchanged in color. If desired, a hair conditioner composition can be applied to the entire head of hair to condition and moisturize the hair. Any hair conditioner is suitable provided it is capable of moisturizing and providing a conditioning effect to the chemically treated hair fibers. Suitable conditioners are typically aqueous based emulsion compositions such as those set forth in U.S. Pat. Nos. 5,989,533 and 6,143,286, both of which are hereby incorporated by reference in their entirety.

The claimed method provides salon quality results in a fast, easy, highlighting procedure that is very adaptable for at home consumer use. It can be used on hair that has been previously colored, and the highlights produced are custom colored.

The Kit

The invention is also directed to a kit for applying highlights to hair comprising (i) a first receptacle containing a oxidizing agent composition, (ii) a second receptacle containing a persulfate composition, (iii) a comb through applicator for attachment to the first or second receptacle; and (iv) a third receptacle containing a colorant composition free of oxidizing agents but containing at least one oxidative dye that will form color on hair when reacted with the oxidizing agent found in the first receptacle composition.

The kit in accordance with the invention is generally depicted in FIG. 5. FIG. 5A shows a box that is a suitable container for the all of the components that may be found in the kit, as further shown in FIGS. 5B, 5C, 5D, and 5F. Boxes are the preferred container for the components of the kit because boxes are cheap and because they are made of paper are environmentally friendly. Nonetheless, other types of containers may be suitable including plastic containers such as pails, boxes, and the like, or even metal containers.

The kit may optionally contain a hair conditioner composition as depicted in FIG. 5E, which is preferably stored in a tube, although a packette form as depicted in FIG. 5G may be a suitable receptacle for storing the hair conditioner composition if it is present in the kit.

Figure 3B:
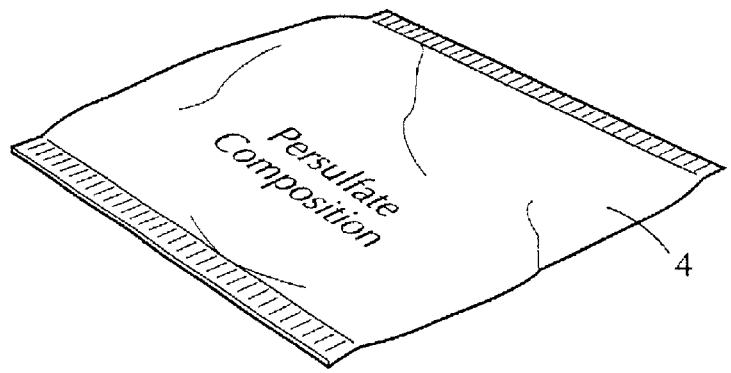
FIG. 3B: is one type of receptacle that may be used for storing the persulfate composition, which is a packette.
Figure 3C:
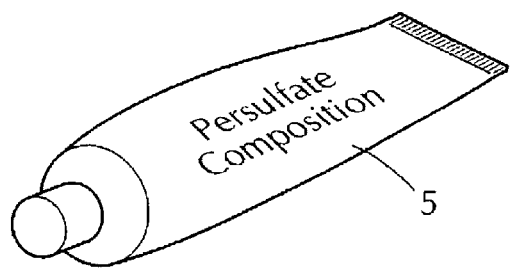
FIG. 3C: is another type of receptacle that may be used for storing the persulfate composition, which is a tube form most preferred when the persulfate composition is in the paste form.
Figure 3D:
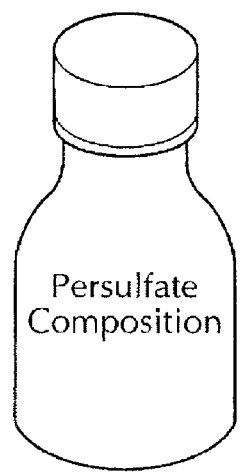
FIG. 3D: is another type of receptacle that may be used to store the persulfate composition. This receptacle is a jar and may be used when the persulfate composition is in the dry powdered form or the paste form, or some other semi-solid or liquid form.

The kit comprises a first receptacle 2 for storing the oxidizing agent composition 1 as best depicted in FIG. 5B. FIG. 5B shows the first receptacle 2 having a lid 2A affixed thereto during storage. Also contained in the kit is a comb on applicator 6, the preferred embodiment of which is depicted in FIG. 5C. Other suitable comb on applicators include those depicted in FIGS. 1A–1E in FIG. 1. The kit further contains a second receptacle that contains the persulfate composition. The persulfate composition may be stored in receptacles as depicted in FIGS. 3A, 3B, and 3C. The packette form 4 is illustrated in FIG. 5D.

The kit further contains a comb on applicator 6 as depicted in FIG. 5C. As previously noted, when the user begins the highlighting process, the cover 2A is removed (see FIG. 3A) from the receptacle 2 containing the oxidizing agent composition 1 as depicted in FIG. 5B and the persulfate composition is combined with the oxidizing agent composition 1. This can be accomplished by pouring the persulfate composition into the receptacle 2 containing the oxidizing agent composition 1, or alternatively, the oxidizing agent composition 1 can be poured into the receptacle containing the persulfate composition 6 if the persulfate composition is contained in a suitable receptacle. The comb on applicator 6 is designed to be affixed to either the receptacle 2 containing the oxidizing agent composition 1 or the receptacle containing the persulfate composition. Preferably, the comb on applicator 6 is designed to be affixed to the receptacle 2 that contains the oxidizing agent composition 1 as depicted in 5B. The comb on applicator 6 is preferably affixed to the receptacle 2 by removing the original lid 2A and attaching the comb on applicator 6. This is done after the oxidizing agent composition and persulfate composition are combined and mixed well. Preferably this is done by incorporating the persulfate composition into the receptacle containing the oxidizing agent composition and reattaching the lid 2A and shaking the receptacle to mix the contents well. Then the lid 2A is removed and the comb on applicator 6 is affixed to the receptacle.

The kit further comprises a colorant composition as described herein, and depicted in FIG. 5F. The colorant composition is preferably contained in a tube, although other forms such as packettes or jars are suitable. The tube form is depicted in FIG. 5E.

If desired, the kit may contain other items such as plastic gloves, instruction booklets, coupons, and other items designed to assist the consumer in the highlighting process.

The compositions, methods and kits are further described in connection with the following examples which are set forth for the purposes of illustration only.

EXAMPLE 1

An oxidizing agent composition in the form of an aqueous hydrogen peroxide based developer was prepared as follows:

|  | w/w % |
| --- | --- |
| EDTA | 0.02 |
| Propylene glycol | 5.00 |
| Laureth-23 | 1.50 |
| Cetearyl alcohol/sodium C12–15 alkyl sulfate | 1.50 |
| Cetearyl alcohol | 1.00 |
| Metaphosphoric acid | 0.25 |
| Disodium phosphate | 0.05 |
| Hydrogen peroxide (35% aqueous solution) | 26.00 |
| Steareth-10 allyl ether methacrylates copolymer | 1.00 |
| Water | QS |

The above mentioned developer composition was prepared by combining the ingredients and mixing well.

EXAMPLE 2

A persulfate composition was prepared according to the following formula:

|  | w/w % |
| --- | --- |
| Potassium persulfate | 50.00 |
| Sodium persulfate | 12.00 |
| Ammonium persulfate | 20.00 |
| Sodium metasilicate | 15.00 |
| Hydrated silica | 1.00 |
| Sodium lauryl sulfate | 1.00 |
| Tetrasodium EDTA | 1.00 |

EXAMPLE 3

A hair colorant composition in the shampoo form for providing red highlights was prepared as follows:

|  | w/w % |
| --- | --- |
| Hydroxypropylmethylcellulose | 0.30 |
| Ethoxydiglycol | 2.00 |
| Erythorbic acid | 0.50 |
| Tetrasodium EDTA | 0.30 |
| Sodium sulfite | 0.50 |
| P-phenylenediamine | 2.00 |
| 2-amino-3-hydroxypyridine | 0.90 |
| Sodium lauryl sulfate (30% aqueous solution) | 10.00 |
| Sodium laureth sulfate (28% aqueous solution) | 20.00 |
| Lauramide DEA (86% aqueous solution) | 2.00 |
| Cocamidopropyl betaine (35% solution) | 4.00 |
| Oleic acid | 6.00 |
| Ethanolamine | 2.50 |
| Fragrance | 0.75 |
| Water | QS |

EXAMPLE 4

A hair colorant composition in the shampoo form for providing brown highlights was prepared as follows:

|  | w/w % |
| --- | --- |
| Hydroxypropylmethylcellulose | 0.03 |
| Ethoxydiglycol | 2.00 |
| Erythorbic acid | 0.50 |
| Tetrasodium EDTA | 0.30 |
| Sodium sulfite | 0.50 |
| P-phenylenediamine | 0.06 |
| Resorcinol | 0.04 |
| 1-naphthol | 0.04 |
| Sodium lauryl sulfate (30% aqueous solution) | 10.00 |
| Sodium laureth sulfate (28% aqueous solution) | 20.00 |
| Lauramide DEA (86% aqueous solution) | 2.00 |
| Cocamidopropyl betaine (35% solution) | 2.00 |
| Oleic acid | 6.00 |
| Ethanolamine | 2.50 |
| Fragrance | 0.50 |
| Water | QS |

EXAMPLE 5

A hair colorant composition in the shampoo form for providing blonde highlights was prepared as follows:

|  | w/w % |
| --- | --- |
| Hydroxypropylmethylcellulose | 0.03 |
| Ethoxydiglycol | 2.00 |
| Erythorbic acid | 0.50 |
| Tetrasodium EDTA | 0.30 |
| Sodium sulfite | 0.50 |
| P-phenylenediamine | 0.001 |
| 1-naphthol | 0.003 |
| Sodium lauryl sulfate (30% aqueous solution) | 10.00 |
| Sodium laureth sulfate (28% aqueous solution) | 20.00 |
| Lauramide DEA (86% aqueous solution) | 2.00 |
| Cocamidopropyl betaine (35% solution) | 2.00 |
| Oleic acid | 6.00 |
| Ethanolamine | 2.50 |
| Fragrance | 0.50 |
| Water | QS |

EXAMPLE 6

Approximately 55 grams of the aqueous oxidizing agent composition of Example 1 was mixed with 20 grams of the persulfate composition of Example 2 to form a bleach composition. The bleach composition was combed through the hair with the comb through applicator attached to the receptacle depicted in FIG. 1F. The bleach composition was left on the hair for 20 minutes, then rinsed off with water for about 1 minute. The entire head of hair was then shampooed with the hair colorant composition of Example 3 for about 2 minutes and rinsed well with water. Hair conditioner was then applied and rinsed out well with water. The hair was towel dried. The hair strands that were treated with the bleach composition exhibited distinct, subtle red highlights while the untreated hair remained the same color as it was prior to the procedure. The treated strands exhibited uniform root to tip highlights.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for altering the color of hair comprising applying a bleach composition containing persulfate salts and at least one oxidizing agent to the desired strands of hair for a period of time sufficient to bleach the hair, removing the bleach composition from the hair but leaving at least some residual oxidizing agent on the bleached hair strands, then treating the hair with a colorant composition containing at least one dye operable to color hair in the presence of the residual oxidizing agent found on the bleached hair strands, said colorant composition being free of any oxidizing agents operable to react with the dye present therein to form color, whereby upon contact with the colorant composition, the hair strands treated with the bleach composition having residual oxidizing agent thereon will react with the dye present in the colorant composition to cause the bleached hair strands to become colored, while any remaining unbleached hair will not become colored by contact with the colorant composition.

2. The method of claim 1 wherein the entire head of hair is colored.

3. The method of claim 1 wherein only select strands of hair are colored.

4. The method of claim 1 wherein the bleach composition is prepared by combining about 10–95 parts of the oxidizing agent composition and about 10 to 95 parts of the persulfate composition.

5. The method of claim 4 wherein the oxidizing agent comprises hydrogen peroxide.

6. The method of claim 5 wherein the oxidizing agent composition is in the form of an emulsion or solution.

7. The method of claim 6 wherein the oxidizing agent composition comprises, by weight of the total oxidizing agent composition, about 1–30% oxidizing agent and about 50–99% water.

8. The method of claim 7 wherein the oxidizing agent composition further comprises about 0.01–30% by weight of the total oxidizing agent composition of an oily phase.

9. The method of claim 1 wherein the persulfate composition is in the particulate or paste form.

10. The method of claim 9 wherein the persulfate composition is in the particulate form.

11. The method of claim 9 wherein the persulfate composition comprises about 10–65% by weight of the total persulfate composition of one or more inorganic persulfates.

12. The method of claim 11 wherein the persulfate composition further comprises about 0.1–40% by weight of the total composition of one or more alkalizing agents.

13. The method of claim 11 wherein the persulfate composition comprises about 5–60% by weight of the total composition of one or more particulate fillers.

14. The method of claim 11 wherein the persulfate composition comprises about 0.1–70% by weight of the total persulfate composition of one or more lipophilic ingredients.

15. The method of claim 1 wherein the bleach composition is applied to the desired strands of hair with a comb on applicator affixed to a receptacle.

16. The method of claim 15 wherein the bleach composition is applied to the hair for about 10 to 65 minutes.

17. The method of claim 1 wherein the bleach composition is removed from the hair by rinsing well with water.

18. The method of claim 17 wherein the hair is rinsed for about 1 to second to five minutes to remove the bleach composition from the hair.

19. The method of claim 1 wherein the hair colorant composition is applied to the hair for about 2 minutes.

20. The method of claim 1 wherein the hair colorant composition comprises, by weight of the total hair colorant composition, about 0.1–99% water and at least one dye.

21. The method of claim 20 wherein the hair colorant composition comprises at least one primary intermediate and, optionally, at least one coupler for the formation of oxidation dyes.

22. The method of claim 20 wherein the hair colorant composition comprises, by weight of the total hair colorant composition, about 0.0001–6% of at least one primary intermediate, and, optionally, about 0.0001–10% of at least one coupler for the formation of oxdiation dyes.

23. The method of claim 20 wherein the hair colorant composition is in the form of a shampoo.

24. The method of claim 23 wherein the hair colorant composition further comprises one or more surfactants.

25. The method of claim 23 wherein the hair colorant composition comprises one or more alkalizing agents present at about 1–5% by weight of the total hair colorant composition.

26. The method of claim 23 wherein the hair colorant composition comprises one or more fatty acids present at about 0.001–15% by weight of the total hair colorant composition.

27. The method of claim 1 wherein the hair colorant composition is removed from the hair by rinsing well with water.

* * * * *